(12) United States Patent
Jakielski et al.

(10) Patent No.: US 9,804,110 B2
(45) Date of Patent: Oct. 31, 2017

(54) MEASUREMENT METHOD FOR DETECTING DAMAGE TO A TURBINE BLADE AND TURBINE

(71) Applicant: Siemens Aktiengesellschaft, Munich (DE)

(72) Inventors: Sebastian Jakielski, Bottrop (DE); Stefan Obermayr, Mulheim (DE)

(73) Assignee: Siemens Aktiengesellschaft, Munich (DE)

( * ) Notice: Subject to any disclaimer, the term of this patent is extended or adjusted under 35 U.S.C. 154(b) by 368 days.

(21) Appl. No.: 14/438,320

(22) PCT Filed: Oct. 1, 2013

(86) PCT No.: PCT/EP2013/070433
§ 371 (c)(1),
(2) Date: Apr. 24, 2015

(87) PCT Pub. No.: WO2014/067737
PCT Pub. Date: May 8, 2014

(65) Prior Publication Data
US 2015/0285753 A1    Oct. 8, 2015

(30) Foreign Application Priority Data
Oct. 31, 2012  (EP) ..................................... 12190744

(51) Int. Cl.
*F01D 21/04*    (2006.01)
*G01N 27/02*    (2006.01)
(Continued)

(52) U.S. Cl.
CPC .............. *G01N 27/025* (2013.01); *F01D 5/14* (2013.01); *F01D 21/003* (2013.01); *G01H 1/006* (2013.01);
(Continued)

(58) Field of Classification Search
CPC ........ G01N 27/025; G01N 27/61; F01D 5/14; F01D 21/003; F01D 21/14; F01D 21/06;
(Continued)

(56) References Cited

U.S. PATENT DOCUMENTS 3,654,803 A    4/1972  Robinson
4,934,192 A    6/1990  Jenkins
(Continued)

FOREIGN PATENT DOCUMENTS

CN    1682013 A    10/2005
CN    1708633 A    12/2005
(Continued)

*Primary Examiner* — Gregory Anderson
*Assistant Examiner* — Eldon Brockman
(74) *Attorney, Agent, or Firm* — Beusse Wolter Sanks & Maire

(57) ABSTRACT

A measurement method for early detection of damage to a blade of an impeller of a turbine is provided. During operation, in a rotational direction of the blade along a circumference which surrounds the impeller, at a plurality of points, in each case a plurality of magnetic fields are generated next to one another substantially in an oscillation direction of the blade, which magnetic fields are influenced by a tip of a turbine blade during transit. Positional values of the tip are detected by at the plurality of points. A positional profile of the turbine blade is then formed from the positional values and a frequency is determined from the positional profile. The frequency is compared with defined frequency values. An alarm event is recognized in case of a sudden and/or pronounced change in the frequency. In addition, a turbine is provided which is configured to carry out the method.

9 Claims, 3 Drawing Sheets

(51) Int. Cl.
  *F01D 21/00*   (2006.01)
  *G01H 1/00*    (2006.01)
  *F01D 5/14*    (2006.01)
  *G01N 27/61*   (2006.01)

(52) U.S. Cl.
  CPC ......... *G01N 27/61* (2013.01); *F05D 2260/80* (2013.01); *F05D 2270/821* (2013.01)

(58) Field of Classification Search
  CPC ................ G01H 1/006; F05D 2260/80; F05D 2270/821
  See application file for complete search history.

(56) References Cited

U.S. PATENT DOCUMENTS

| | | | |
|---|---|---|---|
| 4,951,500 | A | 8/1990 | Osborne |
| 5,206,816 | A * | 4/1993 | Hill ................ G01H 1/006 |
| | | | 702/56 |
| 7,023,205 | B1 | 4/2006 | Krupp |
| 7,521,926 | B2 | 4/2009 | Beck et al. |
| 2004/0060371 | A1 | 4/2004 | Barkhoudarian |
| 2005/0122095 | A1* | 6/2005 | Dooley ................ F01D 17/06 |
| | | | 324/174 |
| 2006/0012377 | A1 | 1/2006 | Bosselmann |
| 2006/0171806 | A1* | 8/2006 | Twerdochlib .......... G01H 1/006 |
| | | | 416/61 |
| 2009/0078053 | A1* | 3/2009 | Twerdochlib .......... G01H 1/006 |
| | | | 73/661 |
| 2009/0314092 | A1* | 12/2009 | Twerdochlib .......... G01H 1/006 |
| | | | 73/659 |
| 2010/0127694 | A1 | 5/2010 | Weickert |
| 2011/0213569 | A1 | 9/2011 | Zielinski et al. |
| 2011/0231171 | A1* | 9/2011 | Jousselin ............... G01H 1/006 |
| | | | 703/7 |

FOREIGN PATENT DOCUMENTS

| | | |
|---|---|---|
| DE | 102008057556 A1 | 5/2010 |
| EP | 1538448 A1 | 6/2005 |
| EP | 2299248 A1 | 3/2011 |
| EP | 2312410 A1 | 4/2011 |
| GB | 2476184 B | 5/2012 |
| JP | H0264206 A | 3/1990 |
| JP | H0763606 A | 3/1995 |
| JP | H1068654 A | 3/1998 |
| JP | 2012501445 A | 1/2012 |
| WO | 2012067781 A1 | 5/2012 |

* cited by examiner

MEASUREMENT METHOD FOR DETECTING DAMAGE TO A TURBINE BLADE AND TURBINE

CROSS REFERENCE TO RELATED APPLICATIONS

This application is the U.S. National Stage of International Application No. PCT/EP2013/070433 filed Oct. 1, 2013, and claims the benefit thereof. The International Application claims the benefit of European Application No. EP12190744 filed Oct. 31, 2012. All of the applications are incorporated by reference herein in their entirety.

FIELD OF INVENTION

The present invention relates to a measurement method for early detection of damage to a blade of an impeller of a turbine and to a turbine.

BACKGROUND OF INVENTION

It is known to examine blades of a turbine for damage by means of eddy current testing. In this case, the probes are moved directly onto the workpiece in order to detect extremely small cracks.

An examination of this kind is not possible during operation of the turbine, on account of the direct contact between the probes and the blades. Damage occurring during operation can thus be determined at the earliest in the testing interval following thereon following completion of the operation.

SUMMARY OF INVENTION

The present invention is based on an object of providing an improved measurement method and a turbine which is constructed in such a way as to carry out this measurement method.

This object is achieved by a method and a turbine as claimed. Advantageous developments of the invention are specified in the sub-claims and described in the description.

In the measurement method according to aspects of the invention for the early detection of damage to a blade of an impeller of a turbine, during operation of the turbine, in a rotational direction of the blade along a circumference which surrounds the impeller, at a plurality of points, in each case a plurality of magnetic fields are generated next to one another substantially in an oscillation direction of the blade, which magnetic fields are influenced by a tip of a blade leaf of the blade during transit. As a result of the influence at the plurality of points, positional values of the tip are required. A positional profile of the blade leaf is then formed from the positional values and a frequency is determined from the positional profile. This frequency is compared with specific frequency values. In the event of a sudden and/or sharp change in the frequency, an alarm event is detected.

The measuring areas each have a plurality of rows of probes arranged next to one another. In particular, the plurality of rows are arranged in relation to one another in a direction which extends at right angles to the direction of oscillation of the blade.

Therefore, in order to detect the position, recourse can be had to redundant data. The acquisition of the positions of the tips of the blade leaves can therefore be carried out more reliably.

The measurement method presented shows one possible way in which permanent real-time vibration measurement can be implemented during operation, in particular of a steam turbine, at the self-supporting end blades, and offers effective protection against turbine damage.

It is advantageously possible, when a crack progresses into the blade root but still considerably before a break in the blade leaf, to determine a frequency change on the relevant blade and thereupon to switch off the turbine early in order to prevent greater damage effectively.

The solution presented comprises both a measurement on all conductive and also on permeable blades. Even blades made of titanium or aluminum can be checked. A volatile magnetization of the blades is not required.

In addition, at the same time effects of variable operating parameters on the blades can be detected and displayed.

Furthermore, the application of the method according to aspects of the invention contributes to higher confidence in turbine technology.

In an advantageous embodiment of the measurement method according to aspects of the invention, the positional values are transferred into a sine curve as a positional profile.

Therefore, one from the wavelength or the frequency of the positional profile is easy to determine. The values for the frequency to be checked can be determined rapidly.

In a further advantageous embodiment of the measurement method according to aspects of the invention, the blades are checked cyclically one after another.

Therefore, in a straightforward way, all the blades of an impeller are subjected regularly to a check. The cycle is so short that no failure of a blade can occur between two checks.

In a further advantageous embodiment of the measurement method according to aspects of the invention, the specific frequency values are determined from the already determined frequencies of the blade.

Therefore, different oscillation characteristics of the individual blades are also taken into account when detecting an alarm event. As a result, the measurement method becomes more accurate. Erroneous messages can therefore be avoided.

In a further advantageous embodiment of the measurement method according to aspects of the invention, the specific frequencies are determined from a previously defined frequency range.

Therefore, even before the turbine is started up for the first time, comparative values are available. The situations in which the measurement method can be used are therefore expanded.

According to aspects of the invention, the turbine, comprising a diffuser and an impeller arranged in the diffuser and having a plurality of blades, comprises measuring areas at a plurality of points along a circumference which surrounds the impeller in a direction of rotation of the blades. These measuring areas each have at least one exciter coil and a plurality of probes which are arranged next to one another substantially in an oscillation direction of the blades and which can be connected to an evaluation unit. The probes are in particular eddy current probes; and the turbine according to aspects of the invention is in particular a steam turbine.

Advantageously, a turbine for the execution of the measurement method according to aspects of the invention is therefore provided. The turbine exhibits increased operational reliability. Incidents caused by damage to the blades can be avoided. Therefore, the turbine itself and the surroundings thereof are protected.

Here, the probes do not protrude and do not influence the flow. A robust and long-lasting device having a high resolving capability and the possibility of permanent online monitoring is provided.

In an advantageous refinement of the turbine according to aspects of the invention, the measuring areas are arranged distributed uniformly over the entire circumference.

Therefore, data about the oscillation behavior of the blades can be determined over the entire circumference. More data is available for evaluation. In addition, in the case of measurements on the entire circumference with the impellers not rotating in a vertical axis, effects of the force of gravity on the oscillation behavior of individual blades can also be established.

In a further advantageous refinement of the turbine according to aspects of the invention, the latter has water cooling on the measuring areas.

This therefore permits effective cooling of the measuring areas, which sets the measuring areas to a more beneficial operating temperature and can therefore increase the functional duration of the measuring areas.

BRIEF DESCRIPTION OF THE DRAWINGS

Exemplary embodiments of the invention will be explained in more detail by using the drawings and the following description. In the drawings.

DETAILED DESCRIPTION OF INVENTION

Figure 1:
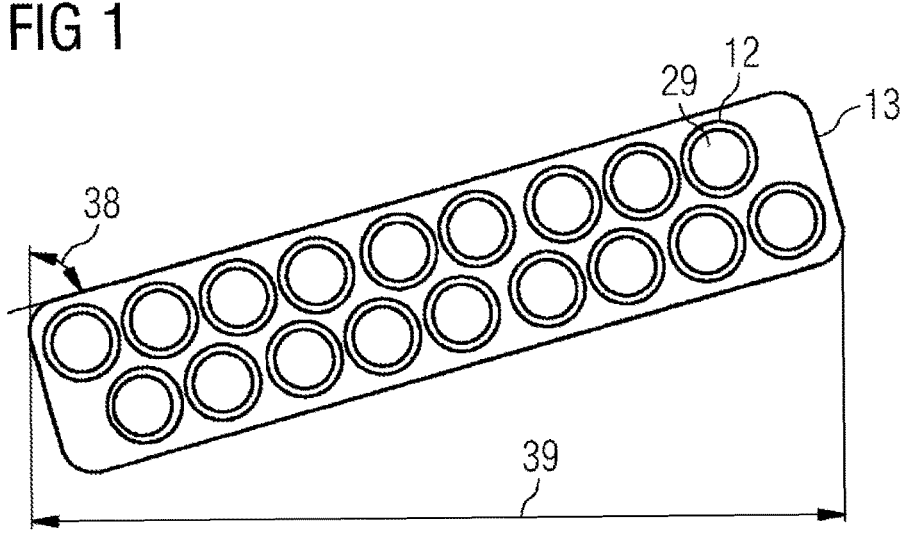
FIG. 1 shows a measuring area of an inventive turbine.

In FIG. 1, a measuring area 13 of an inventive turbine 10 is shown by way of example in a sketch. The measuring area 13 comprises a plurality of probes 12 which are arranged next to one another and which in particular are arranged in a plurality of rows. In particular, exciter coils 29 for generating a variable magnetic field in each case are integrated into the probes 12. The probe 12 is in particular one for the detection of eddy currents.

The measuring area 13 depicted comprises eighteen probes 12. According to aspects of the invention, the number of probes 12 in a measuring area 13 can also be more or less than eighteen.

Depending on the blade type, the measuring area 13 has a measuring width 39 which goes beyond the width of the oscillation amplitude plus blade leaf width. A skew 38 of the measuring area 13 is designed as a function of an oscillation direction 18 of the blades. The distance of the individual probes 12 from one another is likewise designed as a function of the oscillation amplitude. In addition, the shape of the diffuser 16 in which the measuring area 13 is intended to be arranged is taken into account.

The exciter coils 29 provided are relatively small examples, for example with a diameter of 0.5 mm to 2 mm, in order to detect a permeable or electrically conductive blade 26 located in the magnetic field.

In the embodiments described here, use is made of the property that the "lift off signal" on the impedance plane moves when a conductive or permeable test object is located in the active range of the magnetic field.

Depending on the frequency, about 20 Hz to 2 MHz, and the diameter of the exciter coils 29, the blade 26 can be detected as a test object still a few mm away from the probes 12. This distance can be enlarged further by known techniques, such as magnetic shielding and ferrite core.

Figure 2:
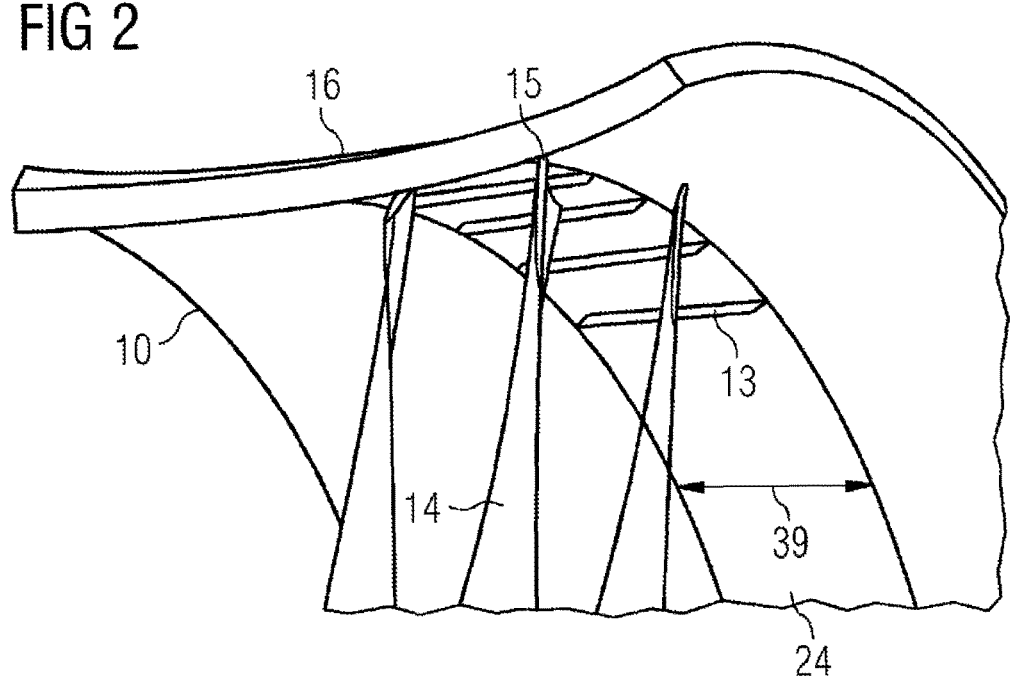
FIG. 2 shows an arrangement of a plurality of measuring areas in the turbine.

In FIG. 2, an arrangement of a plurality of measuring areas 13 in a diffuser 16 of a turbine 10 according to aspects of the invention is illustrated by way of example in a sketch.

The measuring areas 13 are arranged in a fixed manner in the diffuser 16, directly above tips 15 of blade leaves 14 of the blades 26. The measuring areas 13 are in particular positioned at uniform intervals in a circumference 24 of the diffuser 16, which forms an inner side of the diffuser 16 surrounding the blades 26.

The measuring areas 13 here have a measuring width 39 which is greater than a thickness of the blade leaves 14 plus their axial oscillation amplitude. Thus, it is possible to perform a determination of the axial position of the tip with an accuracy of about 0.5 mm to 1 mm.

In order to be able to measure a frequency 22 of the blade leaf 14, it is necessary to arrange a plurality of the measuring areas 13 distributed on the circumference 24. In the measurement method 11, these are activated one after another in synchronism with the rotational speed.

The spacing between the individual measuring areas 13 depends on the frequency of the exciter coil 29, the length of the circumference 24 and the natural oscillation of the blade 26. An exemplary calculation for an exciter frequency of 25 Hz, a circumference of 21 m and a natural oscillation of the blade 26 of 150 Hz, shows a spacing of 0.7 m per measuring area 13 at 5 measuring points:

25 Hz*21 m=525 m/s 525 m/s/150 Hz=3.5 m wavelength 3.5 m/5 measuring points=0.7 m spacing.

The turbine 10 has through-pockets in the diffuser 16 for the individual measuring areas 13. These through-pockets can also be introduced retrospectively if a turbine is to be retrofitted with measuring areas 13. In addition, the turbine 10 according to aspects of the invention has data lines which connect the probes 12 to an evaluation unit.

Optionally, the turbine 10 according to aspects of the invention can have water cooling, with which the exciter coils 29 can be cooled effectively. Thus, a long service life of the exciter coils 29 can be achieved.

Figure 3:
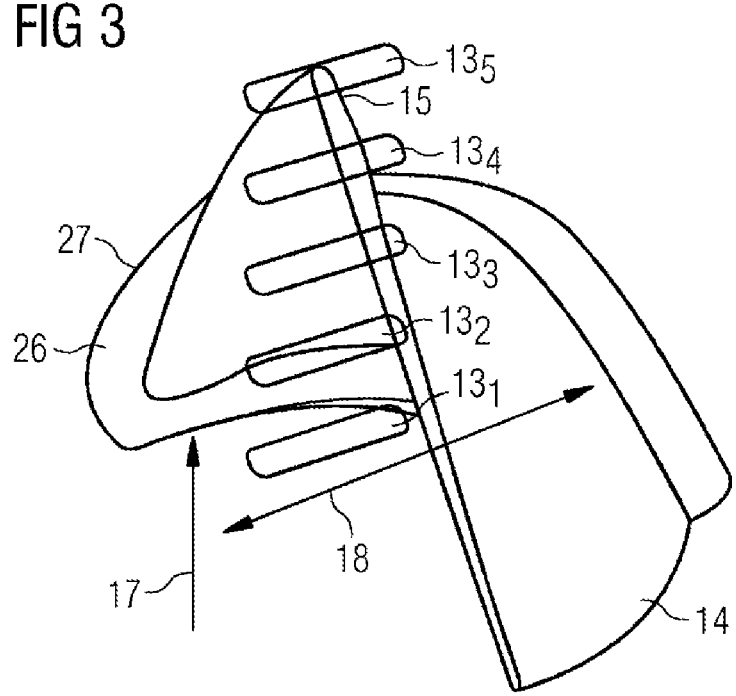
FIG. 3 shows the measuring areas over a blade leaf of the turbine.

FIG. 3 shows, in a sketch and by way of example, the arrangement of a plurality of measuring area 13 over a blade 26 in a plan view. The diffuser 16 is masked out in this illustration.

During operation of the turbine 10, the blade leaf 14 arranged on a blade root 27 moves in the direction of rotation 17 and at the same time oscillates in a direction of oscillation 18.

Along the direction of rotation 17, the measuring areas $13_1$ to $13_5$ are illustrated here by way of example. The measuring areas 13 are arranged parallel to the direction of oscillation 18. They have the same skew 38 with respect to an axis of rotation of the impeller as the direction of oscillation 18. Their measuring width 39 projects over the width of the oscillation amplitude plus the blade leaf width.

During a rotation of the impeller of the turbine 10, the tip 15 of the blade leaf 14 traverses the various measuring areas $13_1$ to $13_5$ one after another. In FIG. 3, the tip 15 is just traversing the measuring area $13_5$. As a result of the oscillation of the blade leaf 14, the tip 15 traverses the various measuring areas 13 at different points of the measuring width 39. This is registered 32 by the probes 12 of the measuring areas 13 at said points, which here, in the example, results in five positional values 19 for the tip 15 of the blade 26.

The measuring areas $13_1$ to $13_5$ are activated one after another, in particular in synchronism with the rotational speed of the impeller, in order to determine from a specific blade 26 in each case the circumference-dependent position change of the tip 15, for example at the steam inlet edge.

The circumferential position must be picked up at an arbitrary point on the rotor in order to be able to measure the blades positionally accurately in the manner of a stroboscope.

Figure 4:
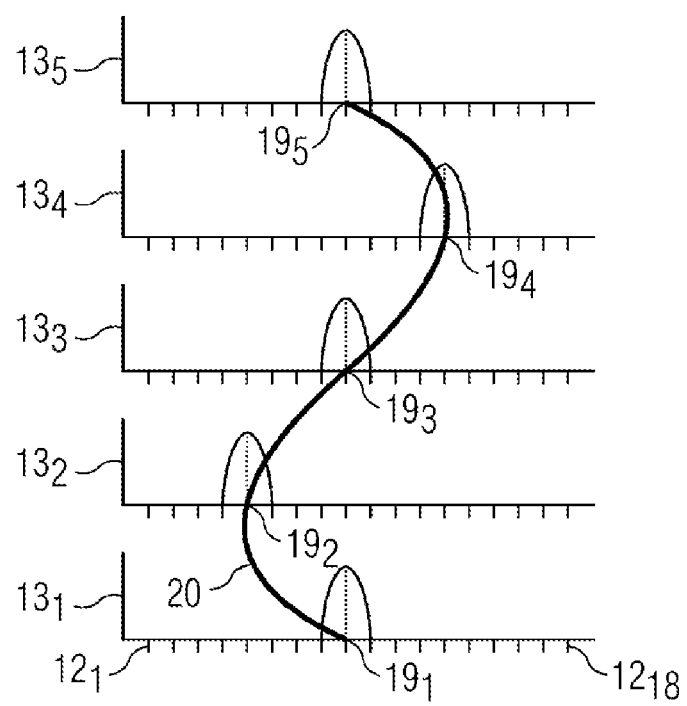
FIG. 4 shows the positional profile of a blade leaf.

From the five positional values 19 of the blade 26 at the five measuring areas $13_1$ to $13_5$, a positional profile 20 is formed 33 by an evaluation unit. Such a positional profile 20 is illustrated by way of example in FIG. 4.

Here, the positional values $19_1$ to $19_5$ for the five different measuring areas $13_1$ to $13_5$ are depicted one after another. Here, the positional values $19_1$ to $19_5$ are registered 32 by eighteen probes $12_1$ to $12_{18}$ for each measuring area 13. The positional values $19_1$ to $19_5$ are converted by the evaluation unit in particular into a sine function. From the latter, a wavelength of the oscillation and, mathematically from the latter, a frequency 22 for the blade 26 are determined 34. The measured result becomes more accurate here with increasing density of measuring points.

In this way, the frequency 22 of each blade 26 is monitored cyclically one after another. In the event of large cracks in the blade root 27, a frequency 22 of the blade changes by a few Hz, which can easily be depicted by the technique according to aspects of the invention. To this end, the frequencies 22 determined are observed over a time 21.

Figure 5:
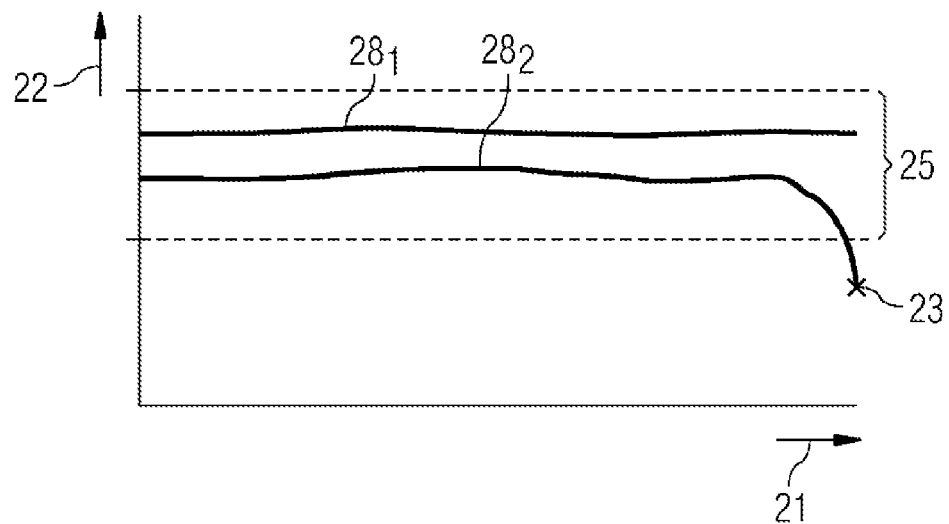
FIG. 5 shows frequency profiles of two blade leaves.

FIG. 5 shows, by way of example, the frequencies 22 depicted over the time 21 in a frequency profile 28. Shown here by way of example are two frequency profiles $28_1$ and $28_2$ of two different blades 26. According to aspects of the invention, in particular the frequencies 22 of all the blades 26 are monitored.

The frequencies 22 obtained are compared 35 with specific frequency values. These frequency values can be obtained, for example, from the previous values of the blade and/or the specific frequency values are predefined values from a specific frequency range 25. In the event of a sudden and/or distinct change in the frequency 22 on one of the blades 26, an alarm event 23 is detected 36 and an alarm is output or the turbine 10 is run down under control.

In FIG. 5, such an alarm event 23 occurs in the lower frequency profile $28_2$.

Figure 6:
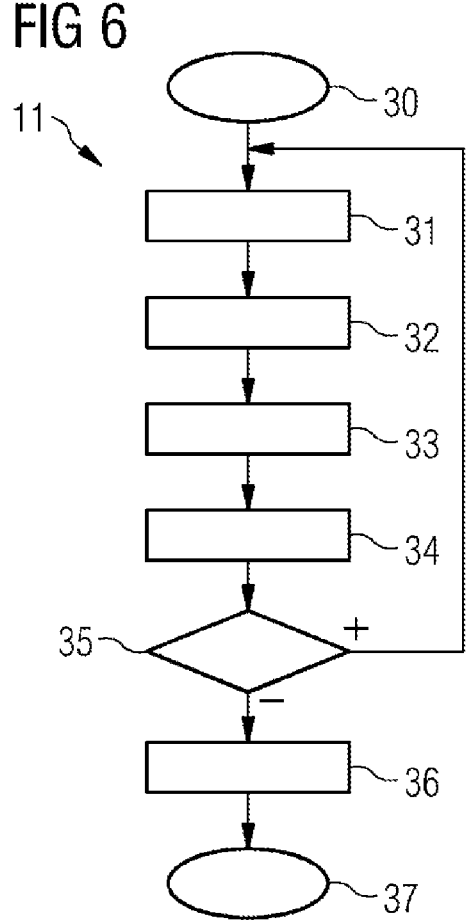
FIG. 6 shows a measurement method according to aspects of the invention.

FIG. 6 shows, by way of example, a measurement method 11 according to aspects of the invention in a flow chart from a start 30 as far as an end 37. In a first step, magnetic fields are generated 31. The tip 15 of the blade 26 traversing the magnetic fields at a specific point influences specific magnetic fields and the positional values 19 of the tip 15 are acquired 32. From the positional values 19, the evaluation unit forms 33 the positional profile 20 and determines 34 the frequency 22 of the positional profile 19. The frequency 22 obtained is then compared 35 with specific frequency values. In this way, all the blades 26 of the turbine 10 are monitored cyclically one after another. If the frequency 22 obtained deviates from the specific frequency values, an alarm event 23 is detected 36. The latter can be used as a starting signal for further safety measures, such as switching off the turbine, for example.

Although the invention has been illustrated and described in more detail by means of the preferred exemplary embodiment, the invention is not restricted by the examples disclosed and other variations can be derived therefrom by those skilled in the art without departing from the protective scope of the invention.

The invention claimed is:

1. A measurement method for the early detection of damage to a blade of an impeller of a turbine, the method comprising
   during operation of the turbine,
   in a rotational direction of the blade along a circumference which surrounds the impeller, at a plurality of points, in each case a plurality of magnetic fields are generated next to one another substantially in an oscillation direction of the blade, which magnetic fields are influenced by a tip of a blade leaf of the blade during transit, wherein, in the turbine, measuring areas are arranged at a plurality of points along the circumference in the direction of rotation, wherein the measuring areas are formed with a plurality of exciter coils and with a plurality of rows of probes arranged next to one another,
   acquiring, as a result of the influence at the plurality of points, positional values of the tip,
   forming a positional profile of the blade leaf from the positional values,
   determining a frequency from the positional profile,
   comparing the frequency with specific frequency values and
   in the event of a sudden and/or sharp change in the frequency, detecting an alarm event.

2. The measurement method as claimed in claim 1, wherein the positional values are transferred into a sine curve as a positional profile.

3. The measurement method as claimed in claim 1, wherein the blades are checked cyclically one after another.

4. The measurement method as claimed in claim 1, wherein the specific frequency values are determined from the already determined frequencies of the blade.

5. The measurement method as claimed in claim 1, wherein the specific frequencies are determined from a previously defined frequency range.

6. A turbine comprising
   a diffuser and an impeller arranged in the diffuser and having a plurality of blades,
   wherein the turbine comprises measuring areas at a plurality of points along a circumference which surrounds the impeller in a direction of rotation of the blades,
   wherein the measuring areas each have with a plurality of exciter coils and a plurality of probes which are arranged next to one another substantially in an oscillation direction of the blades and which can be connected to an evaluation unit,
   wherein the measuring areas each have a plurality of rows of probes arranged next to one another.

7. The turbine as claimed in claim 6, wherein the measuring areas are arranged distributed uniformly over the entire circumference.

8. The turbine as claimed in claim 6, wherein the plurality of rows are arranged in relation to one another in a direction which extends at right angles to the oscillation direction of the blade.

9. The turbine as claimed in claim 6, wherein the turbine has water cooling on the measuring areas.

\* \* \* \* \*